United States Patent [19]
Eyre

[11] Patent Number: 5,962,236
[45] Date of Patent: *Oct. 5, 1999

[54] URINARY ASSAY FOR MEASURING BONE RESORPTION

[75] Inventor: David R. Eyre, Mercer Island, Wash.

[73] Assignee: Washington Research Foundation, Seattle, Wash.

[*] Notice: This patent is subject to a terminal disclaimer.

[21] Appl. No.: 09/209,864

[22] Filed: Dec. 11, 1998

Related U.S. Application Data

[63] Continuation of application No. 09/047,268, Mar. 24, 1998, which is a continuation of application No. 08/771,452, Dec. 20, 1996, abandoned, which is a continuation of application No. 08/497,731, Jun. 21, 1995, Pat. No. 5,607,862, which is a continuation of application No. 08/195,323, Feb. 10, 1994, abandoned, which is a continuation of application No. 07/840,574, Feb. 24, 1992, abandoned, which is a continuation of application No. 07/592,511, Oct. 3, 1990, abandoned, which is a division of application No. 07/118,234, Nov. 6, 1987, Pat. No. 4,973,666.

[51] Int. Cl.⁶ .................................................. G01N 33/53
[52] U.S. Cl. ........................... 435/7.1; 435/7.9; 435/7.92; 436/518; 436/531
[58] Field of Search ........................... 435/7.1, 7.9, 7.92; 436/518, 531

[56] References Cited

U.S. PATENT DOCUMENTS

| | | |
|---|---|---|
| 4,628,027 | 12/1986 | Gay . |
| 4,973,666 | 11/1990 | Eyre . |
| 5,607,862 | 3/1997 | Eyre . |

OTHER PUBLICATIONS

Eyre, D.R., "Crosslink maturation in bone collagen," In: Veis, A., ed. the *Chemistry and Biology of Mineralized Connective Tissues*, Elsevier North Holland, Inc., 1981.

Gunja–Smith, Z. and Boucek, R.J., "Collagen cross–linking compounds in human urine," *Biochemical Journal*, 197:759–762 (1981).

Barber, M., et al., "The structure(s) of pyridinoline(s)," *Biochemical and Biophysical Research Communications*, 109(3):1041–1046, 1982.

Ogawa, T., et al., "A novel fluor in insoluble collagen: a crosslinking moiety in collagen molecule," *Biochemical and Biophysical Research Communications*, 104(4:1252–1257, 1982.

Eyre, D.R., "Collagen cross–linking," In: Akeson, W.H. et al., eds., *AAOS: Symposium on Heritable Disorders of Connective Tissue*, St. Louis: C.V. Mosby, 1982, pp. 43–58.

Robins, S.P., "An enzyme–linked immunoassay for the collagen cross–link pyridinoline," *Biochemical Journal*, 207:617–620 (1982).

Fujimoto, D., et al., "Analysis of Pyridinoline, a Cross–Linking Compound of Collagen Fibers, in Human Urine," *J. Biochem.*, 94:1133–1136 (1983).

Eyre, D.R., et al., "Cross–Linking in Collagen and Elastin," *Ann. Rev. Biochem.*, 53:717–748 (1984).

Eyre, D.R., et al., "Quantitation of Hydroxypyridinium Crosslinks in Collagen by High–Performance Liquid Chromatography," *Analytical Biochemistry*, 137:380–388 (1984).

Wu, et al., "Identification of Hydroxypyridinium Cross–Linking Sites in Type II Collagen of Bovine Articular Cartilage," *Biochemistry* 23:1850–1857 (1984).

Wu, et al., "Cartilage type IX collagen is cross–linked by hydroxypyridinium residues," *Biochemical and Biophysical Research Communications* 123(3):1033–1039 (1984).

Robins, S.R., et al., "Measurement of the cross linking compound, pyridinoline, in urine as an index of collagen degradation in joint disease," *Annals of the Rheumatic Diseases*, 45:969–973 (1986).

Eyre, D., "Collagen Cross–Linking Amino Acids," In: *Methods in Enzymology*, vol. 144, pp. 115–139, Academic Press, Inc., 1987.

Eyre, D.R., "Collagen Stability Through Covalent Crosslinking," In: Pearson, et al., eds. *Advances in Meat Research, vol. 4, Collagen as a Food*. New York: Van Nostrand Reinhold, 1987.

Robins, S., et al., "Pyridinium crosslinks of bone collagen and their location in peptides isolated from rat femur," *Biochemica et Biophysica Acta*, 914(3):233–239, 1987.

Robins, S.P., et al., "Measurement of Hydroxypyridinium Crosslinks of Collagen as an Index of Bone Matrix Degradation," *Abstract*, Lake Garda, Italy (1987).

Macek, J., et al., "Determination of collagen degradation products in human urine in osteoporosis," *Z. Rheumatol.*, 46:237–240, 1987.

*Primary Examiner*—Jeffrey Stucker
*Attorney, Agent, or Firm*—Christensen, O'Connor, Johnson & Kindness PLLC

[57] ABSTRACT

Urinary assay for measuring bone resorption, by contacting an unhydrolyzed urine sample with an antibody that binds to free lysyl pyridinoline cross-links, detecting any binding of the antibody in the body fluid sample, and correlating the detected binding to bone resorption in vivo. The free lysyl pyridinoline cross-links are preferably measured as a ratio to the creatinine content in order to provide a urinary index of bone resorption independent of urine volume.

2 Claims, 4 Drawing Sheets

FLUORESCENCE 297nm, 380nm

FLUORESCENCE Ex 297nm, Em 380nm

URINARY ASSAY FOR MEASURING BONE RESORPTION

This application is a continuation of prior application Ser. No. 09/047,268 filed Mar. 24, 1998, which is a continuation of Ser. No. 08/771,452 filed Dec. 20, 1996, now abandoned, which is a continuation of Ser. No. 08/497,731 filed Jun. 21, 1995, now U.S. Pat. No. 5,607,862, which is a continuation of Ser. No. 08/195,323 filed Feb. 10, 1994, which is a continuation of Ser. No. 07/840,574 filed Feb. 24, 1992, now abandoned, which is a continuation of Ser. No. 07/592,511 filed Oct. 3, 1990, now abandoned, which is a divisional of Ser. No. 07/118,234 filed Nov. 6, 1987, now U.S. Pat. No. 4,973,666.

This invention relates to a method for assaying bone resorption rates. More specifically, it relates to a method for quantitating specific urinary cross-linking amino acids, and peptide fragments that contain those amino acids derived from degraded bone collagen.

BACKGROUND OF THE INVENTION

Osteoporosis is the most common bone disease in man. Primary osteoporosis, with increased susceptibility to fractures, results from a progressive net loss of skeletal bone mass. It is estimated to affect 15–20 million individuals in the United States. Its basis is an age-dependent imbalance in bone remodelling, i.e., in the rates of synthesis and degradation of bone tissue. About 1.2 million osteoporosis-related fractures occur in the elderly each year including about 538,000 compression fractures of the spine, about 227,000 hip fractures and a substantial number of early fractured peripheral bones. Twelve to 20% of the hip fractures are fatal because they cause severe trauma and bleeding, and half of the surviving patients require nursing home care. Total costs from osteoporosis-related injuries now amount to at least $7 billion annually (Barnes, O. M., Science, 236, 914 (1987)). Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, no method is available for measuring bone resorption rates in patients or normal subjects. A major difficulty in monitoring the disease is the lack of a specific assay for measuring bone resorption rates.

Methods for assessing bone mass often rely on measuring whole-body calcium by neutron activation analysis or mineral mass in a given bone by photon absorption techniques. These measurements can give only long-term impressions of whether bone mass is decreasing. Measuring calcium balances by comparing intake with output is tedious, unreliable and can only indirectly appraise whether bone mineral is being lost over the long term. Other methods currently available for assessing decreased bone mass and altered bone metabolism include quantitative scanning radiometry at selected bone locations (wrist, calcaneus, etc.) and histomorphometry of iliac crest biopsies. The former provides a crude measure of the bone mineral content at a specific site in a single bone. Histomorphometry gives a semi-quantitative assessment of the balance between newly deposited bone seams and resorbing surfaces.

A urinary assay for the whole-body output of degraded bone in 24 hours would be much more useful. Mineral studies (e.g., calcium balance) cannot do this reliably or easily. Since bone resorption involves degradation of the mineral and the organic matrix, a specific biochemical marker for newly degraded bone products in body fluids would be the ideal index. Several potential organic indices have been tested. For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased. For this reason, urinary hydroxyproline has been used extensively as an amino acid marker for collagen degradation. Singer, F. R., et al. (1978) In: *Metabolic Bone Disease*, Vol. II (eds. Avioli, L. V. and Krane, S. M.) pp. 489–575, Academic Press, New York.

Goverde (U.S. Pat. No. 3,600,132) discloses a process for determination of hydroxyproline in body fluids such as serum, urine, lumbar fluid and other intercellular fluids in order to monitor deviations in collagen metabolism. In particular, this inventor notes that in pathologic conditions such as Paget's disease, Marfan's syndrome, osteogenesis imperfecta, neoplastic growth in collagen tissues and in various forms of dwarfism, increased collagen anabolism or catabolism as measured by hydroxyproline content in biological fluids can be determined. This inventor measures hydroxyproline by oxidizing it to a pyrrole compound with hydrogen peroxide and N-chloro-p-toluenesulphonamide followed by calorimetric determination in p-dimethyl-amino-benzaldehyde.

In the case of Paget's disease, the increased urinary hydroxyproline probably comes largely from bone degradation, hydroxyproline, however, generally cannot be used as a specific index. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline. Furthermore, about 80% of the free hydroxyproline derived from protein degradation is metabolized in the liver and never appears in the urine. Kiviriko, K. I. (1970) *Int. Rev. Connect. Tissue Res.* 5, 93, and Weiss, P. H. and Klein, L. (1969) *J. Clin. Invest.* 48, 1.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption. Krane, S. M. and Simon, L. S. (1981) *Develop. Biochem.* 22, 185.

In addition to amino acids unique to collagen, various non-collagenous proteins of bone matrix such as osteocalcin, or their breakdown products, have formed the basis of immunoassays aimed at measuring bone metabolism. Price, P. A. et al. (1980) *J. Clin. Invest.* 66, 878, and Gundberg, C. M. et al. (1984) *Meth. Enzymol.* 107, 516. However, it is now clear that bone-derived non-collagenous proteins, though potentially a useful index of bone metabolic activity are unlikely, on their own, to provide quantitative measures of bone resorption. The concentration in serum of osteocalcin, for example, fluctuates quite widely both normally and in metabolic bone disease. Its concentration is elevated in states of high skeletal turnover but it is unclear whether this results from increased synthesis or degradation of bone. Krane, S. M., et al. (1981) *Develop. Biochem.* 22, 185, Price, P. A. et al. (1980) *J. Clin. Invest.* 66, 878, and Gundberg, C. M. et al. (1984) *Meth. Enzymol.* 107, 516.

Collagen Cross-Linking

The polymers of most genetic types of vertebrate collagen require the formation of aldehyde-mediated cross-links for normal function. Collagen aldehydes are derived from a few specific lysine or hydroxylysine side-chains by the action of lysyl oxidase. Various di-, tri- and tetrafunctional cross-linking amino acids are formed by the spontaneous intra- and intermolecular reactions of these aldehydes within the newly formed collagen polymers; the type of cross-linking residue varies specifically with tissue type (see Eyre, D. R. et al. (1984) *Ann. Rev. Biochem.* 53: 717–748). Two basic pathways of cross-linking can be differentiated for the banded (67 nm repeat) fibrillar collagens, one based on lysine aldehydes, the other on hydroxylysine aldehydes. The lysine aldehyde pathway dominates in adult skin, cornea, sclera, and rat tail tendon and also frequently occurs in other soft connective tissues. The hydroxylysine aldehyde pathway dominates in bone, cartilage, ligament, most tendons and most internal connective tissues of the body, Eyre, D. R. et al. (1974) vida supra. The operating pathway is governed by whether lysine residues are hydroxylated in the telopeptide sites where aldehyde residues will later be formed by lysyl oxidase (Barnes, M. J. et al. (1974) *Biochem. J.* 139, 461). The chemical structure(s) of the mature cross-linking amino acids on the lysine aldehyde pathway are unknown, but hydroxypyridinium residues have been identified as mature products on the hydroxylysine aldehyde route. On both pathways and in most tissues the intermediate, borohydride-reducible cross-linking residues disappear as the newly formed collagen matures, suggesting that they are relatively short-lived intermediates (Bailey, A. J. et al. (1971) *FEBS Lett.* 16, 86). Exceptions are bone and dentin, where the reducible residues persist in appreciable concentration throughout life, in part apparently because the rapid mineralization of the newly made collagen fibrils inhibits further spontaneous cross-linking interactions (Eyre, D. R. (1981) In: *The Chemistry and Biology of Mineralized Connective Tissues* (Veis, A. ed.) pp. 51–55, Elsevier, New York, and Walters, C. et al. (1983) *Calc. Tiss. Intl.* 35: 401–405).

Two chemical forms of 3-hydroxypyridinium cross-link have been identified (Formula I and II). Both compounds are naturally fluorescent, with the same characteristic excitation and emission spectra (Fujimoto, D. et al. (1977) *Biochem. Biophys. Res. Commun.* 76, 1124, and Eyre, D. R. (1981) *Develop. Biochem.* 22, 50). These amino acids can be resolved and assayed directly in tissue hydrolysates with good sensitivity using reverse phase HPLC and fluorescence detection. Eyre, D. R. et al. (1984) *Analyt. Biochem.* 137: 380–388.

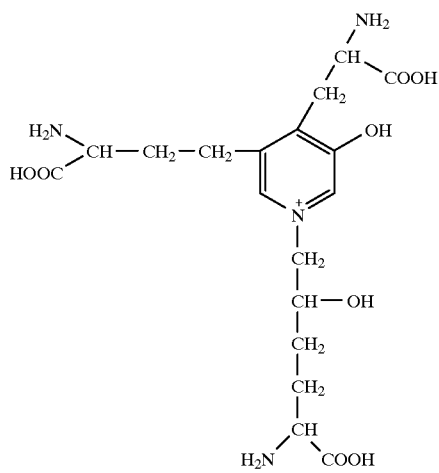

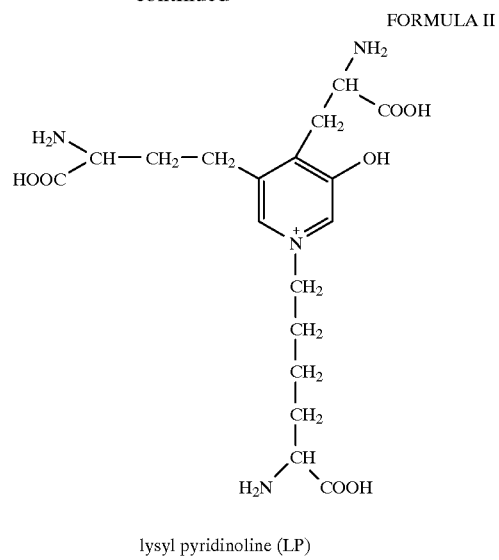

lysyl pyridinoline (LP)

In growing animals it has been reported that these mature cross-links may be concentrated more in an unmineralized fraction of bone collagen than in the mineralized collagen (Banes, A. J., et al. (1983) *Biochem. Biophys. Res. Commun.* 113, 1975). However, other studies on young bovine or adult human bone do not support this concept, Eyre, D. R. (1985) In: *The Chemistry and Biology of Mineralized Tissues* (Butler, W. T. ed.) p 105, Ebsco Media Inc., Birmingham, Ala.

The presence of collagen hydroxypyridinium cross-links in human urine was first reported by Gunja-Smith and Boucek (Gunja-Smith, Z. and Boucek, R. J. (1981) *Biochem J.* 197: 759–762) using lengthy isolation procedures for peptides and conventional amino acid analysis. At that time, they were aware only of the HP form of the cross-link. Robins (Robins, S. P. (1982) *Biochem J.* 207: 617–620) has reported an enzyme-linked immunoassay to measure HP in urine, having raised polyclonal antibodies to the free amino acid conjugated to bovine serum albumin. This assay is intended to provide an index for monitoring increased joint destruction that occurs with arthritic diseases and is based, according to Robins, on the finding that pyridinoline is much more prevalent in cartilage than in bone collagen. In more recent work involving enzyme-linked immunoassay, Robins reports that lysyl pyridinoline is unreactive toward antiserum to pyridinoline covalently linked to bovine serum albumin (Robins et al. (1986) *Ann. Rheum. Diseases* 45, 969–973). Robins' urinary index for cartilage destruction is based on the discovery that hydroxylysyl pyridinoline, derived primarily from cartilage, is found in urine at concentrations proportional to the rate of joint cartilage resorption. In principal, this index could be used to measure whole body cartilage loss, however, no information on bone resorption would be available.

A need therefore exists for a method that allows the measurement of whole-body bone resorption rates in humans. The most useful such method would be one that could be applied to body fluids, especially urine. The method should be sensitive, i.e., quantifiable down to 1 picomole and rapidly measure 24-hour bone resorption rates so that the progress of various therapies (e.g., estrogen) can be assessed.

SUMMARY OF THE INVENTION

A method for determining the absolute rate of bone resorption comprising quantitating the concentration of peptide fragments having 3-hydroxypyridinium cross-links derived from bone collagen resorption in a body fluid. The quantitating steps consists of contacting the body fluid with an immunological binding partner specific to a peptide fragment having 3-hydroxypyridinium cross-links derived from bone collagen resorption. In one embodiment of the invention, the body fluid is optionally purified prior to the contacting step. This purification step is selected from a number of standard procedures, including cartridge adsorption and elution, molecular sieve chromatography, dialysis, ion exchange, alumina chromatography, hydroxyapatite chromatography, and combinations thereof.

The invention also encompasses other methods for quantitating the concentration of peptide fragments having 3-hydroxypyridinium cross-links in a body fluid. These methods include electrochemical titration, natural fluorescence spectroscopy, and ultraviolet absorbance. Electrochemical titration may be conducted directly upon a body fluid without further purification. However, when this is not possible due to excessive quantities of contaminating substances, the body fluid is first purified prior to the electrochemical titration step. Suitable methods for purification prior to electrochemical detection include dialysis, ion exchange chromatography, alumina chromatography, molecular sieve chromatography, hydroxyapatite chromatography and ion exchange absorption and elution.

Fluorometric measurement of a body fluid containing 3-hydroxypyridinium cross-links is an alternative way of quantitating bone resorption. The fluorometric assay can be conducted directly on a body fluid without further purification. However, for certain body fluids, particularly urine, it is preferred that purification of the body fluid be conducted prior to fluorometric assay. This purification step consists of dialyzing an aliquot of urine against an aqueous solution thereby producing partially purified peptide fragments retained within the nondiffusate. The nondiffusate is then lyophylized, dissolved in an ion pairing solution and absorbed onto an affinity chromatography column. The chromatography column is washed with a volume of ion pairing solution and, thereafter, the peptide fragments are eluted from the column with an eluting solution. These purified peptide fragments are then hydrolyzed and the hydrolyzate is resolved chromatographically. Chromatographic resolution is conducted by either high-performance liquid chromatography or microbore high performance liquid chromatography.

The invention includes a peptide fragment derived from bone collagen substantially free from other human peptides obtained from a body fluid. The peptide fragment may contain 3-hydroxypyridinium cross-links, in particular, lysyl pyridinoline cross-links and hydroxylysyl pyridinoline cross-links.

A specific peptide fragment having a 3-hydroxypyridinium cross-link derived from the aminoterminal telopeptide domain of bone type I collagen has the following amino acid sequence.

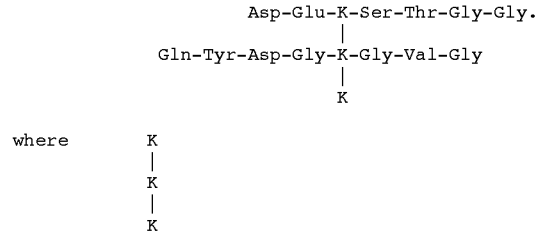

is hydroxylysyl pyridinoline or lysyl pyridinoline and, Gln is glutamine or wholly cyclized pyrrolidone carboxylic acid.

The invention also encompasses a peptide fragment containing 3-hydroxypyridinium cross-links derived from the carboxyterminal telopeptide domain of bone type I collagen. These carboxyterminal telopeptide sequences are cross-linked with either lysyl pyridinoline or hydroxylysyl pyridinoline. An example of such a peptide sequence is represented by the formula:

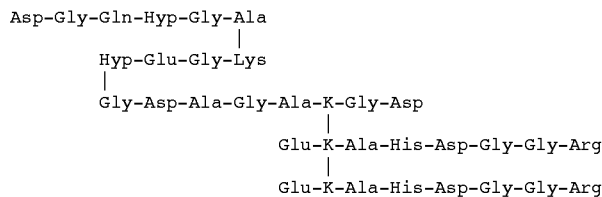

is hydroxylysyl or lysyl pyridinoline.

The invention includes a fused cell hybrid which produces monoclonal antibodies specific for the peptide fragment derived from bone collagen having 3-hydroxypyridinium cross-links. The invention also includes monoclonal antibodies produced by the fused cell hybrid including those antibodies coupled to a detectable marker. Examples of detectable markers include enzymes, chromophores, fluorophores, coenzymes, enzyme inhibitors, chemiluminescent materials, paramagnetic metals, spin labels and radio nucleotides. The invention includes a test kit useful for quantitating the amount of peptide fragments having 3-hydroxypyridinium cross-links derived from bone collagen resorption found in a body fluid comprising the monoclonal antibody specific for peptide fragments derived from bone collagen and containing 3-hydroxypyridinium cross-links. The monoclonal antibodies of this test kit may be coupled to the detectable markers described above.

DETAILED DESCRIPTION OF THE PREFERRED EMBODIMENTS

This invention is based on the discovery that both lysyl pyridinoline (LP) and hydroxylysyl pyridinoline (HP) peptide fragments derived from reabsorbed bone collagen are excreted in the urine without being metabolized. The invention is also based on the discovery that no other connective tissues contain significant levels of LP and that the ratio of HP to LP in mature bone collagen remains relatively constant over a person's lifetime.

Figure 1:
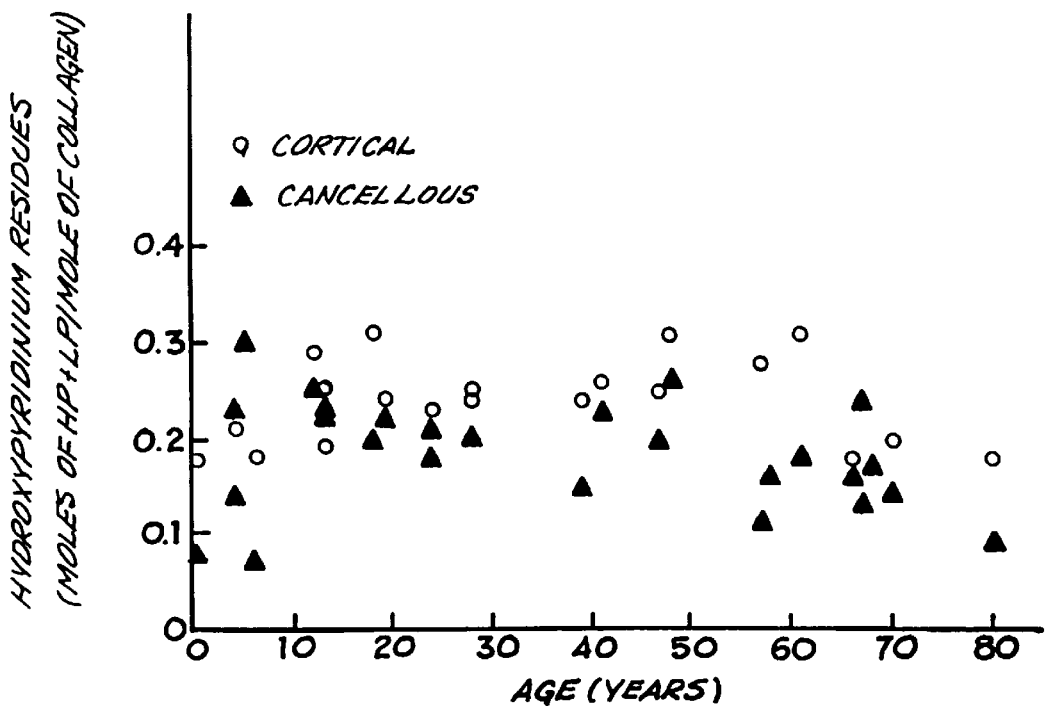
Figure 2:
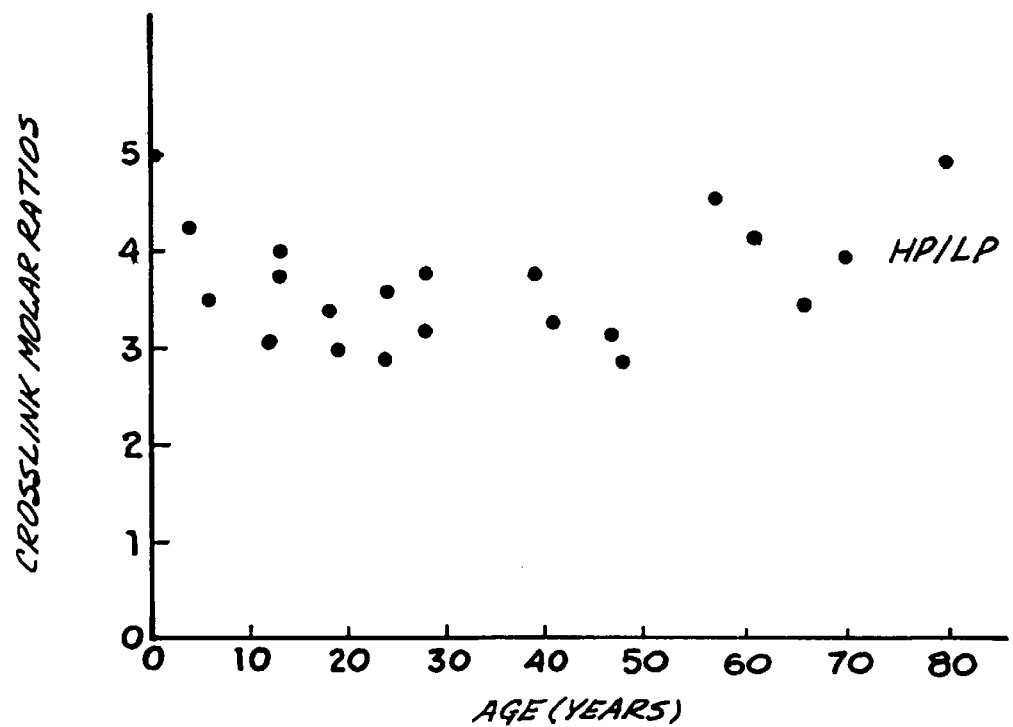

FIG. 1 compares the concentration of HP and LP in both cortical and cancellous human bone with age. It is observed that the concentration of HP plus LP cross-links in bone collagen reaches a maximum by age 10 to 15 years and remains reasonably constant throughout adult life. Furthermore, the ratio of HP to LP, shown in FIG. 2, shows little change throughout life, remaining constant at about 3.5 to 1. These baseline data demonstrate that the 3-hydroxypyridinium cross-links in bone collagen remains relatively constant and therefore that body fluids derived from bone collagen degradation will contain 3-hydroxypyridinium cross-linked peptide fragments at concentrations proportional to the absolute rate of bone resorption.

Since LP is the 3-hydroxypyridinium cross-link unique to bone collagen, the method for determining the absolute rate of bone resorption, in its simplest form, is based on quantitating the concentration of peptide fragments containing 3-hydroxypyridinium cross-links and preferably lysyl pyridinoline (LP) cross-links in a body fluid. As used in this description and in the appended claims, by quantitating is meant measuring by any suitable means, including but not limited to spectrophotometric, gravimetric, volumetric, coulometric, immunometric, potentiometric, or amperometric means the concentration of peptide fragments containing 3-hydroxypyridinium cross-links in an aliquot of a body fluid. Suitable body fluids include urine, serum, and synovial fluid. The preferred body fluid is urine.

Since the concentration of urinary peptides will decrease as the volume of urine increases, it is further preferred that when urine is the body fluid selected, the aliquot assayed be from a combined pool of urine collected over a fixed period of time, for example, 24 hours. In this way, the absolute rate of bone resorption is calculated for a 24 hour period. Alternatively, urinary peptides may be measured as a ratio relative to a marker substance found in urine such as creatinine. In this way the urinary index of bone resorption would remain independent of urine volume.

In one embodiment of the present invention, monoclonal or polyclonal antibodies are produced which are specific to the peptide fragments containing lysyl pyridinoline cross-links found in urine. Peptide fragments may be isolated from the urine of any patient, however, it is preferred that these peptides are isolated from patients with Paget's disease, due to the high concentration of peptide fragments found in these patients.

ISOLATION OF URINARY PEPTIDES

Figure 3A:
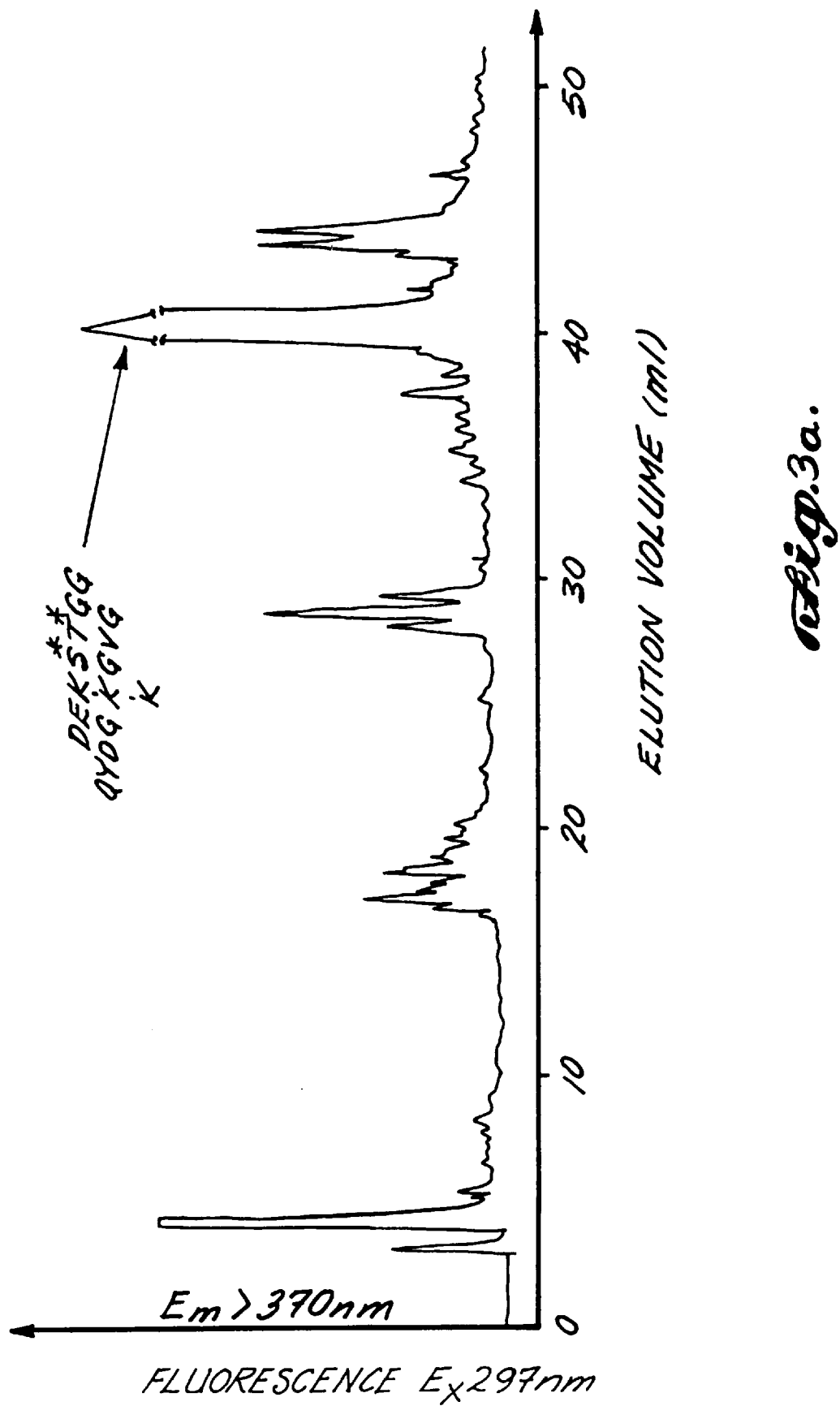

Urine from patients with active Paget's disease is dialyzed in reduced porosity dialysis tubing (>3,500 Spectropore) at 4° C. for 48 h to remove bulk solutes. Under these conditions the peptides of interest are largely retained. The freeze-dried non-diffusate is then eluted (200 mg aliquots) from a column (90 cm×2.5 cm) of Bio-Gel P2 (200–400 mesh) in 10% acetic acid at room temperature. A region of effluent that combines the cross-linked peptides is defined by measuring the fluorescence of collected fractions at 297 nm excitation/ 395 nm emission, and this pool is freeze-dried. Further resolution of this material is obtained on a column of Bio-Gel P-4 (200–400 mesh, 90 cm×2.5 cm) eluted in 10% acetic acid. Two contiguous fraction pools are defined by monitoring the fluorescence of the eluant above. The earlier fraction is enriched in peptide fragments having two amino acid sequences that derive from the carboxyterminal telopeptide domain of the aI(I) chain of bone type I collagen linked to a third sequence derived from the triple-helical body of bone type I collagen. These three peptide sequences are cross-linked with 3-hydroxypyridinium. The overlapping later fraction is enriched in peptide fragments having an amino acid sequence that derives from the aminoterminal telopeptide domain of bone type I collagen linked through a 3-hydroxypyridinium cross-links. Individual peptides are then resolved from each of the two fractions obtained above by ion-exchange HPLC on a TSK DEAE-5-PW column (Bio Rad 7.5 cm×7.5 mm) eluting with a gradient of NaCl (0–0.2M) in 0.02M Tris-HCl, pH 7.5 containing 10% (v/v) acetonitrile. The aminoterminal telopeptide-based and carboxyterminal telopeptide-based cross-linked peptides elute in a series of 3–4 peaks of fluorescence between 0.08M and 0.15M NaCl. The carboxyterminal telopeptide-based cross-linked peptides elute first as a series of fluorescent peaks, and the major and minor aminoterminal telopeptide-based cross-linked peptides elute towards the end of the gradient as characteristic peaks. Each of these is collected, freeze-dried and chromatographed on a C-18 reverse phase HPLC column (Vydac 218TP54, 25 cm×4.6 mm) eluted with a gradient (0–10%) of acetonitrile: n-propanol (3:1 v/v) in 0.01M trifluoroacetic acid. About 100–500 $\mu$g of individual peptide fragments containing 3-hydroxypyridinium cross-links can be isolated by this procedure from a single 24 h collection of Paget's urine. Amino acid compositions of the major isolated peptides confirmed purity and molecular sizes by the whole number stoichiometry of recovered amino acids. Aminoterminal sequence analysis by Edman degradation confirmed the basic core structures suspected from the sequences of the known cross-linking sites in type I collagen and from the matching amino acid compositions. The aminoterminal telopeptide sequence of the α2(I) chain was blocked from sequencing analysis due presumably to the known cyclization of the aminoterminal glutamine to pyrrolidone carboxylic acid. A typical elution profile of aminoterminal telopeptides obtained by the above procedure is shown in FIG. 3a. The major peptide fragment obtained has an amino acid composition: $(Asx)_2(Glx)_2$ $(Gly)_5$Val-Tyr-Ser-Thr, where Asx is the amino acid Asp or Asn and Glx is the amino acid Gln or Glu. The sequence of this peptide is represented by Formula III below.

Figure 3B:
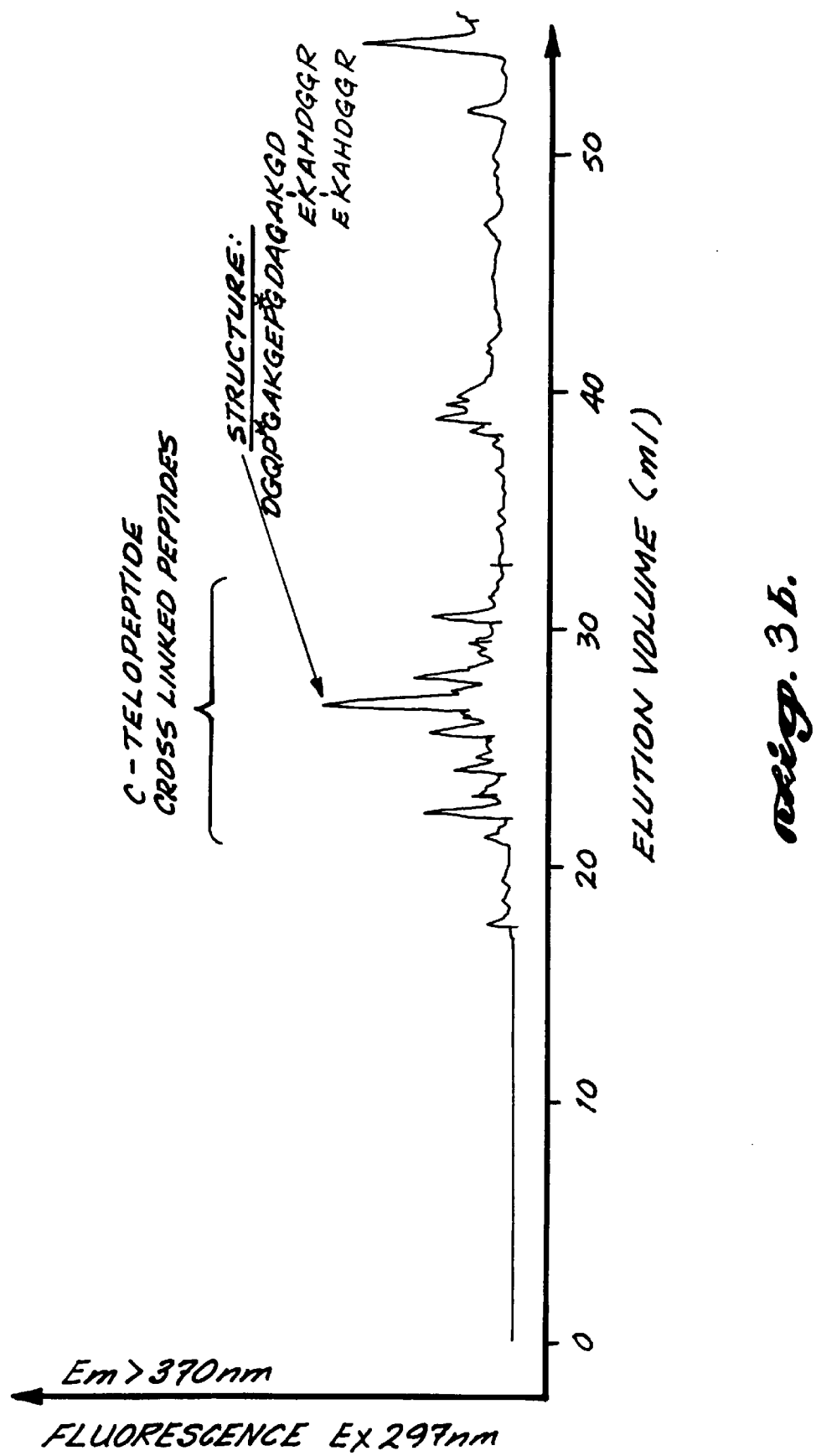

The carboxyterminal telopeptide-based cross-linked peptides resolved by reverse phase HPLC as described above are shown in FIG. 3b. As can be seen from this figure, these peptides are further resolved into a series of carboxyterminal telopeptides each containing the 3-hydroxypyridinium cross-links. The major peptide, shown in FIG. 3b, was analyzed as described above and was found to have the amino acid composition: $(Asp)_5(Glu)_4(Gly)_{10}(His)_2(Arg)_2$ $(Hyp)_2(Ala)_5$. The sequence of this peptide is represented by formula IV below. It is believed that the other carboxyterminal telopeptide-based cross-linked peptides appearing as minor peaks in FIG. 3b represent additions and deletions of amino acids to the structure shown in Formula IV. Any of the peptides contained within these minor peaks are suitable for use as immunogens as described below.

FORMULA III

```
Asp-Glu-K-Ser-Thr-Gly-Gly
         |
Gln-Tyr-Asp-Gly-K-Gly-Val-Gly
         |
         K
```

FORMULA IV

```
Asp-Gly-Gln-Hyp-Gly-Ala
         |
    Hyp-Glu-Gly-Lys
    |
    Gly-Asp-Ala-Gly-Ala-K-Gly-Asp
                       |
              Glu-K-Ala-His-Asp-Gly-Gly-Arg
                   |
              Glu-K-Ala-His-Asp-Gly-Gly-Arg
``` where

```
K
|
K
|
K
``` represents the HP or LP cross-linking amino acids, and

Gln represents glutamine or a wholly cyclized pyrrolidone carboxylic acid.

Equivalents of the peptides represented by the above structures include those cases where some variation in the urinary peptide structure accrues. Examples of variation include amino acid additions to the N and C termini of Formulae III and IV as well as some terminal amino acid deletions. Smaller peptide fragments of the molecule represented by Formula IV derived from bone readsorption are especially evident in urine. These are found in the minor peaks of the carboxytelopeptide fraction seen in FIG. 3b and can be identified by amino acid composition and sequence analysis. Furthermore, both the Ser and Thr residues of Formula III are occasionally conjugated to a small molecule. It is anticipated that antibodies produced to the haptens represented by Formulae III and IV will cross react with urinary peptides of slightly varied structure. In some situations it may be desirable to produce patient-specific antibodies to the urinary peptides derived from bone resorption. In these cases the same procedure described above is utilized to isolate urinary peptides whose structure may vary slightly from that represented by Formulae III and IV.

IMMUNOLOGICAL PROCEDURE FOR INDEXING BONE RESORPTION

Immunological binding partners capable of specifically binding to peptide fragments derived from bone collagen obtained from a physiological fluid can be prepared by methods well known in the art. The preferred method for isolating these peptide fragments is described above. By immunological binding partners as used herein is meant antibodies and antibody fragments.

Both monoclonal and polyclonal antibodies specifically binding the peptides represented by Formulae III and IV and their equivalents are prepared by methods known in the art. For example, *Laboratory Techniques in Biochemistry and Molecular Biology*, Campbell, A. M. (1986) Vol. 13 Elsevier, herein incorporated by reference. It is possible to produce antibodies to the above peptides or their equivalents as isolated. However, because the molecular weights of these peptide fragments are less than 5,000, it is preferred that the hapten be conjugated to a carrier molecule. Suitable carrier molecules include, but are not limited to, bovine serum albumin, ovalbumin, thyroglobulin, and keyhole limpet hemocyanin (KLH). Preferred carriers are thyroglobulin and KLH.

It is well known in the art that the orientation of the hapten, as it is bound to the carrier protein, is of critical importance to the specificity of the anti-serum. Furthermore, not all hapten-protein conjugates are equally successful immunogens. The selection of a protocol for binding the particular hapten to the carrier protein therefore depends on the amino acid sequence of the urinary peptide fragments selected. For example, if the urinary peptide fragment represented by Formula III is selected, a preferred protocol would involve coupling this hapten to keyhole limpet hemocyanin (KLH), or other suitable carrier, with carbodiimide. This would ensure that most of the hapten would be conjugated through the Gly carboxyterminus, thereby presenting the preferred epitope, namely Tyr and 3-hydroxypyridinium cross-link, to the primed vertebrate antibody producing cells (e.g., B-lymphocytes).

Other urinary peptide fragments, depending on the source, may require different binding protocols. Accordingly, a number of binding agents may be suitably employed. These include, but are not limited to, carbodiimides, glutaraldehyde, mixed anhydrides, as well as both homobifunctional and heterobifunctional reagents (see for example the Pierce 1986–87 catalog, Pierce Chemical Co., Rockford, Ill.). Preferred binding agents include carbodiimides and heterobifunctional reagents such as m-Maleimidobenzyl-N-hydroxysuccinimide ester (MBS).

Methods for binding the hapten to the carrier molecule are known in the art. See for example *Laboratory Techniques in Biochemistry and Molecular Biology*, Chard, T. (1987) Vol. 6, Partz Elsevier, N.Y., herein incorporated by reference.

Either monoclonal or polyclonal antibodies to the hapten-carrier molecule immunogen can be produced. However, it is preferred that monoclonal antibodies (MAb) be prepared. For this reason it is preferred that immunization be carried out in the mouse. Immunization protocols for the mouse usually include an adjuvant. Examples of suitable protocols are described by Chard, T. (1987) vida supra. Spleen cells from the immunized mouse are harvested and homogenized and thereafter fused with cancer cells in the presence of polyethylene glycol to produce a fused cell hybrid which produces monoclonal antibodies specific to peptide fragments derived from bone collagen. Examples of such peptide fragments are represented by Formulae III and IV above. Suitable cancer cells include myeloma, hepatoma, carcinoma, and sarcoma cells. Detailed descriptions of this procedure, including screening protocols, protocols for growing selected hybrid cells and harvesting monoclonal antibodies produced by the selected hybrid cells are provided in Galfre, G. and Milstein, C. (1981) *Meth. Enzymol.* 73, 1. A preferred preliminary screening protocol involves the use of peptide fragments derived from bone collagen resorption and containing 3-hydroxypyridinium cross-links in a solid phase radioimmunoassay.

Immunological binding partners, especially monoclonal antibodies, produced by the above procedures, or equivalent procedures, are employed in various immunometric assays to quantitate the concentration of peptide fragments having 3-hydroxypyridinium cross-links derived from bone collagen resorption in body fluids. These immunometric assays comprise a monoclonal antibody or antibody fragment coupled to a detectable marker. Examples of suitable detectable markers include but are not limited to: enzymes, coenzymes, enzyme inhibitors, chromophores, fluorophores, chemiluminescent materials, paramagnetic metals, spin labels, and radionuclides. Examples of standard immunometric methods suitable for indexing bone resorption include, but are not limited to, enzyme linked immunosorbent assay ELISA (Ingvall, E. (1981) Meth. Enzymol. 70), radio-immunoassay (RIA), and "sandwich" Immuno radiometric assay (IRMA). In its simplest form, these immunometric methods can be used to determine the absolute rate of bone resorption by simply contacting a body fluid with the immunological binding partner specific to a peptide fragment having 3-hydroxypyridinium cross-links derived from bone collagen resorption. It is preferred that the immunometric assays described above be conducted directly on untreated body fluids. Occasionally, however, contaminating substances may interfere with the assay necessitating partial purification of the body fluid. Partial purification procedures include, but are not limited to, cartridge adsorption and elution, molecular sieve chromatography, dialysis, ion exchange, alumina chromatography, hydroxyapatite chromatography and combinations thereof.

Test kits, suitable for use in accordance with the present invention, contain monoclonal antibodies prepared as described above that specifically bind to peptide fragments having 3-hydroxypyridinium cross-links derived from bone collagen resorption found in a body fluid. It is preferred that the monoclonal antibodies of this test kit be coupled to a detectable marker of the type described above.

ELECTROCHEMICAL PROCEDURE FOR INDEXING BONE RESORPTION

An alternative procedure for indexing bone resorption consists of measuring a physical property of the peptide fragments having 3-hydroxypyridinium cross-links. One such physical property suitable for indexing bone resorption relies upon electrochemical detection. This method consists of injecting an aliquot of a body fluid, such as urine, into an electrochemical detector poised at a redox potential suitable for detection of peptides containing the 3-hydroxypyridinium ring. The 3-hydroxypyridinium ring, being a phenol, is subject to reversible oxidation and therefore the electrochemical detector (e.g., Model 5100A Coulochem sold by esa 45 Wiggins Ave., Bedford, Mass.) is a highly desirable instrument suitable for quantitating the concentration of urinary peptides derived from bone adsorption. Two basic forms of electrochemical detector are currently commercially available: amperometric (e.g., BioAnalytical Systems) and coulometric (ESA, Inc., Bedford, Mass. 01730). Both are suitable for use in accordance with the present invention, however, the latter system is inherently more sensitive and therefore preferred since complete oxidation or reduction of the analyzed molecule in the column effluent is achieved. In addition, screening or guard electrodes can be placed "upstream" from the analytical electrode to selectively oxidize or reduce interfering substances thereby greatly improving selectivity. Essentially, the voltage of the analytical electrode is tuned to the redox potential of the sample molecule, and one or more pre-treatment cells are set to destroy interferents in the sample. In a preferred assay method, a standard current/voltage curve is established for standard peptides containing lysyl pyridinoline or hydroxylysyl pyridinoline in order to determine the proper voltage to set for optimal sensitivity. This voltage is then modified depending upon the body fluid, to minimize interference from contaminants and optimize sensitivity. Electrochemical detectors, and the optimum conditions for their use are known to those skilled in the art. Complex mixtures of body fluids can often be directly analyzed with the electrochemical detector without interference. Accordingly, for most patients no pretreatment of the body fluid is necessary. In some cases however, interfering compounds may reduce the reliability of the measurements. In such cases, pretreatment of the body fluid (e.g., urine) may be necessary.

Accordingly, in an alternative embodiment of the invention, a body fluid is first purified prior to electrochemically titrating the purified peptide fragments. The purification step may be conducted in a variety of ways including but not limited to; dialysis, ion exchange chromatography, alumina chromatography, hydroxyapatite chromatography, molecular sieve chromatography, or combinations thereof. In a preferred purification protocol, a measured aliquot (25 ml) of a 24 hour urine sample is dialyzed in reduced porosity dialysis tubing to remove the bulk of contaminating fluorescent solutes. The non-diffusate is then lyophilized, redissolved in 1% heptafluorobutyric acid (HFBA), an ion pairing solution, and the peptides adsorbed on a Waters Sep-Pak C-18 cartridge. This cartridge is then washed with 5 ml of 1% HFBA, and then eluted with 3 ml of 50% methanol in 1% HFBA.

Another preferred method of purification consists of adsorbing a measured aliquot of urine onto an ion-exchange adsorption filter and eluting the adsorption filter with a buffered eluting solution. The eluate fractions containing peptide fragments having 3-hydroxypyridinium cross-links are then collected to be assayed.

Still another preferred method of purification employs molecular sieve chromatography. For example, an aliquot of urine is applied to a Bio-Gel P2 or Sephadex G-20 column and the fraction eluting in the 1000–5000 Dalton range is collected. It will be obvious to those skilled in the art that a combination of the above methods may be used to purify or partially purify urine or other body fluids in order to isolate the peptide fragments having 3-hydroxypyridinium cross-links. The purified or partially purified peptide fragments obtained by the above procedures may be subjected to additional purification procedures, further processed or assayed directly in the partially purified state. Additional purification procedures include resolving partially purified peptide fragments employing high performance liquid chromatography (HPLC) or microbore HPLC when increased sensitivity is desired. These peptides may then be quantitated by electrochemical titration. A preferred electrochemical titration protocol consists of tuning the redox potential of the detecting cell of the electrochemical detector (Coulochem Model 5100A) for maximum signal with pure HP. The detector is then used to monitor the effluent from a C-18 HPLC column used to resolve the partially purified urinary peptides.

FLUOROMETRIC PROCEDURE FOR INDEXING BONE RESORPTION

An alternative preferred method for quantitating the concentration of peptide fragments having 3-hydroxypyridinium cross-links is to measure the characteristic natural fluorescence of these peptide fragments. For those body fluids containing few naturally occurring fluorescent materials other than the 3-hydroxypyridinium cross-links, fluorometric assay may be conducted directly without further purification of the body fluid. In this case, peptide fragments are resolved by HPLC and the natural fluorescence of the HP and LP amino acid residues is measured at 395 nm upon excitation at 297 nm, essentially as described by Eyre, D. R., et al., Analyl. Biochem. 137, 380 (1984), herein incorporated by reference.

It is preferred, in accordance with the present invention, that the fluorometric assay be conducted on urine. Urine, however, usually contains substantial amounts of naturally occurring fluorescent contaminants that must be removed prior to conducting the fluorometric assay. Accordingly, urine samples are first partially purified as described above for electrochemical detection. This partially purified urine sample can then be fluorometrically assayed as described above. Alternatively, the HP and LP cross-linked peptides in the partially purified urine samples or other body fluids can be hydrolyzed in 6M HCl at about 108° C. for approximately 24 hours as described by Eyre, et al. (1984) vida supra. This process hydrolyzes the amino acids connected to the lysine precursors of "tripeptide" HP and LP cross-links, producing the free HP and LP amino acids represented by Formulae I and II. These small "tripeptides" are then resolved by the techniques described above, preferably by HPLC, and the natural fluorescence is measured (Ex 297 nm, Ex 390 nm).

Optionally, the body fluid (preferably urine) is passed directly through a C-18 reverse phase affinity cartridge after adding acetonitrile/methanol 5 to 10% v/v. The non-retentate is adjusted to 0.05–0.10M with a cationic ion-pairing agent such as tetrabutyl ammonium hydroxide and passed through a second C-18 reverse phase cartridge. The washed retentate, containing fluorescent peptides, from this second cartridge is eluted with acetonitrile:water (or methanol:water), dried and fluorescent peptides are analyzed by reverse phase HPLC or microbore HPLC using an anionic ion-pairing agent such as 0.01M trifluoroacetic acid in the eluant.

Figure 4B:
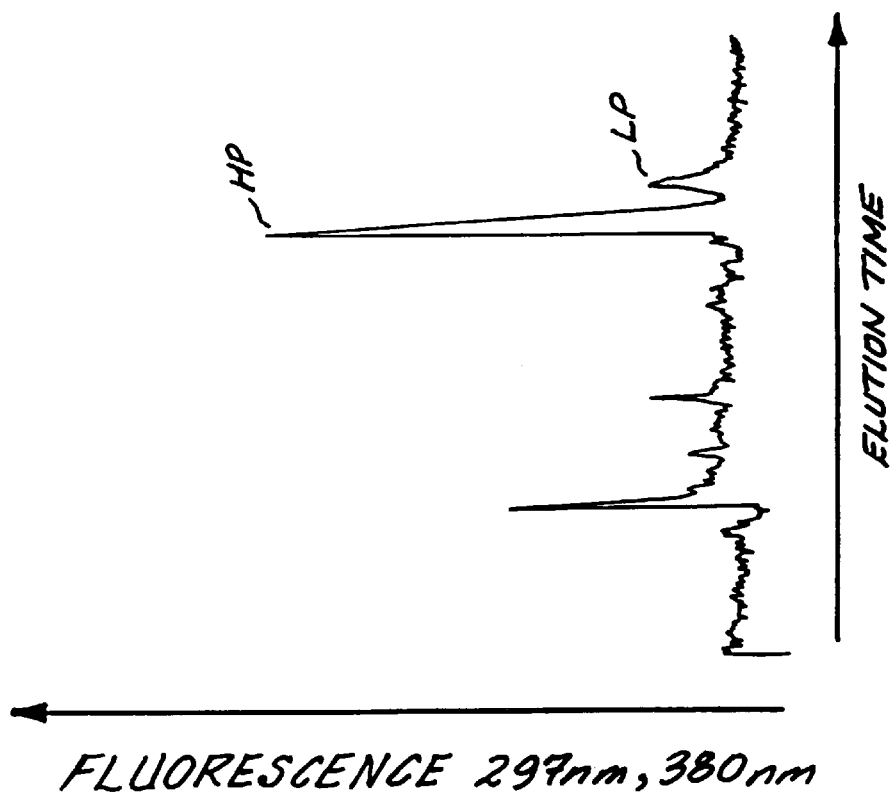
Figure 4A:
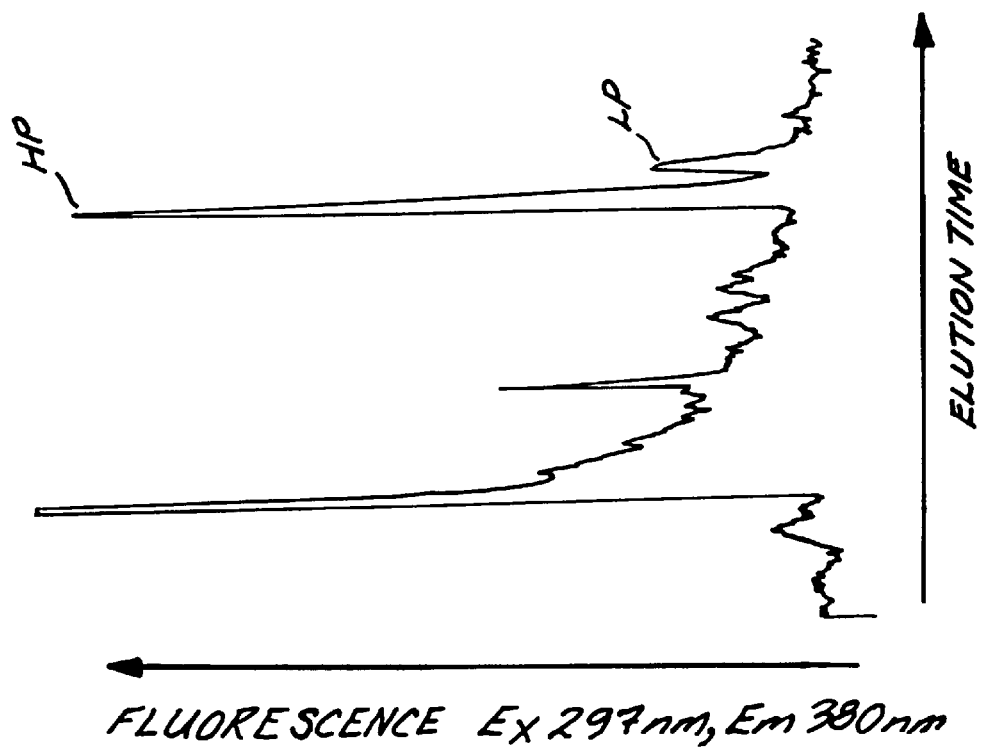

FIG. 4A displays the elution profile resolved by reverse phase HPLC of natural fluorescence for a hydrolysate of peptide fragments from normal human urine. Measurement of the integrated area within the envelope of a given component is used to determine the concentration of that component within the sample. The ratio of HP:LP found in normal human urine and urine from patients having Paget's disease, FIG. 4B, are both approximately 4.5:1. This is slightly higher than the 4:1 ratio found in bone itself (Eyre, et al., 1984). The higher ratio found in urine indicates that a portion of the HP fraction in urine may come from sources other than bone such as the diet, or other sources of collagen degradation, i.e., cartilage catabolism. It is for this reason that it is preferred that LP which derives only from bone be used to provide an absolute index of bone resorption. However, in the absence of excessive cartilage degradation such as in rheumatoid arthritis or in cases where bone is rapidly being absorbed, HP or a combination of HP plus LP may be used as an index of bone resorption.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. In a method of analyzing a body fluid sample for the presence of an analyte indicative of a physiological condition, comprising the steps of contacting the body fluid sample with an immunological binding partner which is capable of binding to the analyte, detecting any binding of the immunological binding partner in the body fluid sample, and correlating the detected binding to bone resorption in vivo, wherein the immunological binding partner is capable of binding to free lysyl pyridinoline cross-links and the body fluid sample is an unhydrolyzed urine sample.

2. The method of claim 1, further comprising the steps of determining the creatinine content of the unhydrolyzed urine sample and determining the ratio of the detected binding to the creatinine content in order to provide a urinary index of free lysyl pyridinoline cross-links independent of urine volume.

* * * * *